(12) United States Patent
Durocher et al.

(10) Patent No.: US 10,499,509 B1
(45) Date of Patent: Dec. 3, 2019

(54) METHODS AND SYSTEMS FOR A FLEXIBLE CIRCUIT

(71) Applicant: General Electric Company, Schenectady, NY (US)

(72) Inventors: Kevin Matthew Durocher, Waterford, NY (US); David Joseph Andrews, Glenville, NY (US); Mark Stephen Maggio, Phoenix, AZ (US); Min Yuan, Watervliet, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/237,269

(22) Filed: Dec. 31, 2018

(51) Int. Cl.
| | |
|---|---|
| *H05K 1/18* | (2006.01) |
| *H05K 3/04* | (2006.01) |
| *H05K 3/24* | (2006.01) |
| *H01L 41/047* | (2006.01) |
| *H01L 41/338* | (2013.01) |
| *H04R 17/00* | (2006.01) |
| *H01L 41/083* | (2006.01) |
| *A61B 8/00* | (2006.01) |

(52) U.S. Cl.
CPC ......... *H05K 1/189* (2013.01); *H01L 41/0475* (2013.01); *H01L 41/083* (2013.01); *H01L 41/338* (2013.01); *H04R 17/00* (2013.01); *H05K 3/041* (2013.01); *H05K 3/241* (2013.01); *A61B 8/4483* (2013.01); *H05K 2201/09509* (2013.01); *H05K 2201/10083* (2013.01)

(58) Field of Classification Search
USPC ....................................................... 361/748
See application file for complete search history.

(56) References Cited

U.S. PATENT DOCUMENTS

| | | | |
|---|---|---|---|
| 8,826,528 B2 * | 9/2014 | Theiss ............... | H01L 21/76802 29/842 |
| 2009/0040415 A1 * | 2/2009 | Kim .................... | G02F 1/13452 349/56 |
| 2013/0257224 A1 | 10/2013 | Wodnicki et al. | |

\* cited by examiner

*Primary Examiner* — Andargie M Aychillhum
(74) *Attorney, Agent, or Firm* — McCoy Russell LLP

(57) ABSTRACT

Various methods and systems are provided for forming a flexible circuit. In one example, a method includes forming a flexible circuit comprising a plurality of contact pads arranged into a plurality of rows, each contact pad of a given row electrically coupled to one another via electrical traces and each contact pad including a via, electroplating the flexible circuit, including electroplating each via, with at least a first material, and upon confirming connectivity of each via, cutting at least some of the electrical traces at least partially.

4 Claims, 11 Drawing Sheets

METHODS AND SYSTEMS FOR A FLEXIBLE CIRCUIT

FIELD

Embodiments of the subject matter disclosed herein relate to flexible circuits for use in ultrasound transducer arrays, and more specifically to testing flexible circuit interconnects.

BACKGROUND

Ultrasonic transducer assemblies are typically employed in applications including non-destructive evaluation (NDE) and medical diagnostic imaging, such as ultrasound applications and computed tomography (CT). The ultrasonic transducer assembly generally includes an array of ultrasonic transducers coupled to an electronics array. The ultrasonic transducer array generally includes hundreds or thousands of individual transducers. Piezoelectric transducers (for example, PZT) are a widely used type of ultrasonic transducer. Piezoelectric sensors generally include a piezoelectric material capable of changing physical dimensions when subjected to electrical or mechanical stress. In addition, piezoelectric sensors may include layers of matching materials and damping materials.

Similarly, the electronics array includes hundreds or thousands of integrated interface circuits (or "cells") which are electrically coupled to provide electrical control of the transducers for beam forming, signal amplification, control functions, signal processing, etc. In particular, each transducer sub-array in the transducer array is typically coupled to an integrated circuit chip to provide individual control of each sensor. In some examples, communication between the integrated circuit chip and the transducers may occur via a flexible circuit that includes a high density of interconnects.

BRIEF DESCRIPTION

In one embodiment, a method includes forming a flexible circuit comprising a plurality of contact pads arranged into a plurality of rows, each contact pad of a given row electrically coupled to one another via electrical traces and each contact pad including a via, electroplating the flexible circuit, including electroplating each via, with at least a first material, and upon confirming connectivity of each via, cutting at least some of the electrical traces at least partially.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
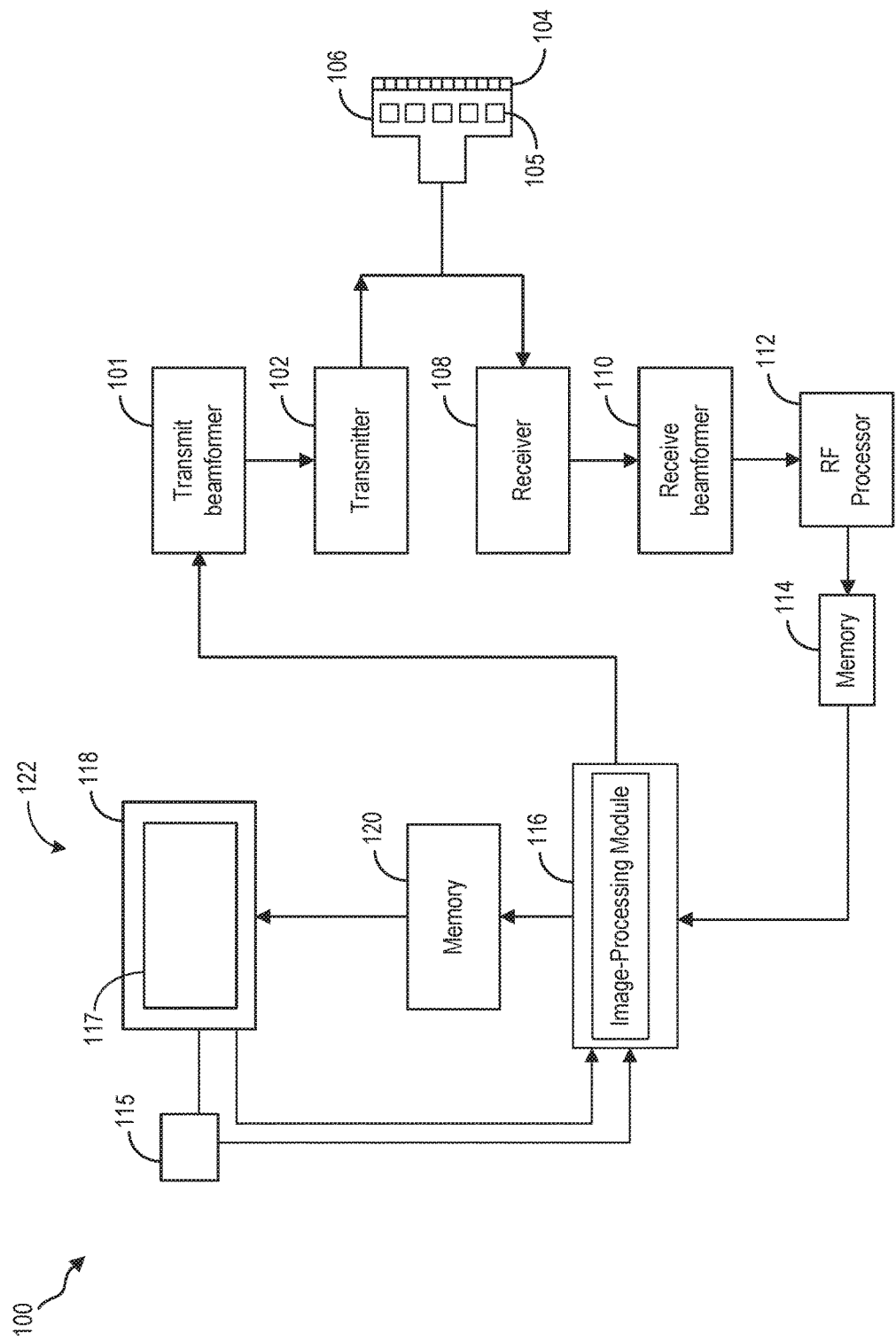
FIG. 1 shows an example ultrasonic imaging system according to an embodiment of the invention.
Figure 2:
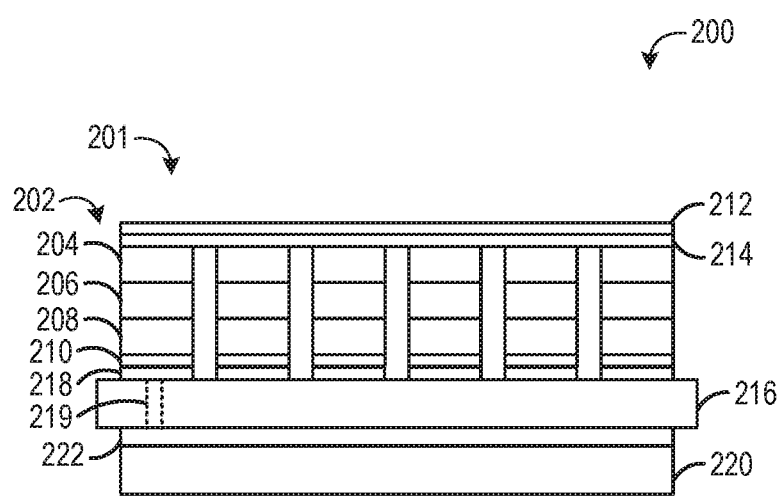
FIG. 2 shows an example ultrasound transducer array.
Figure 3:
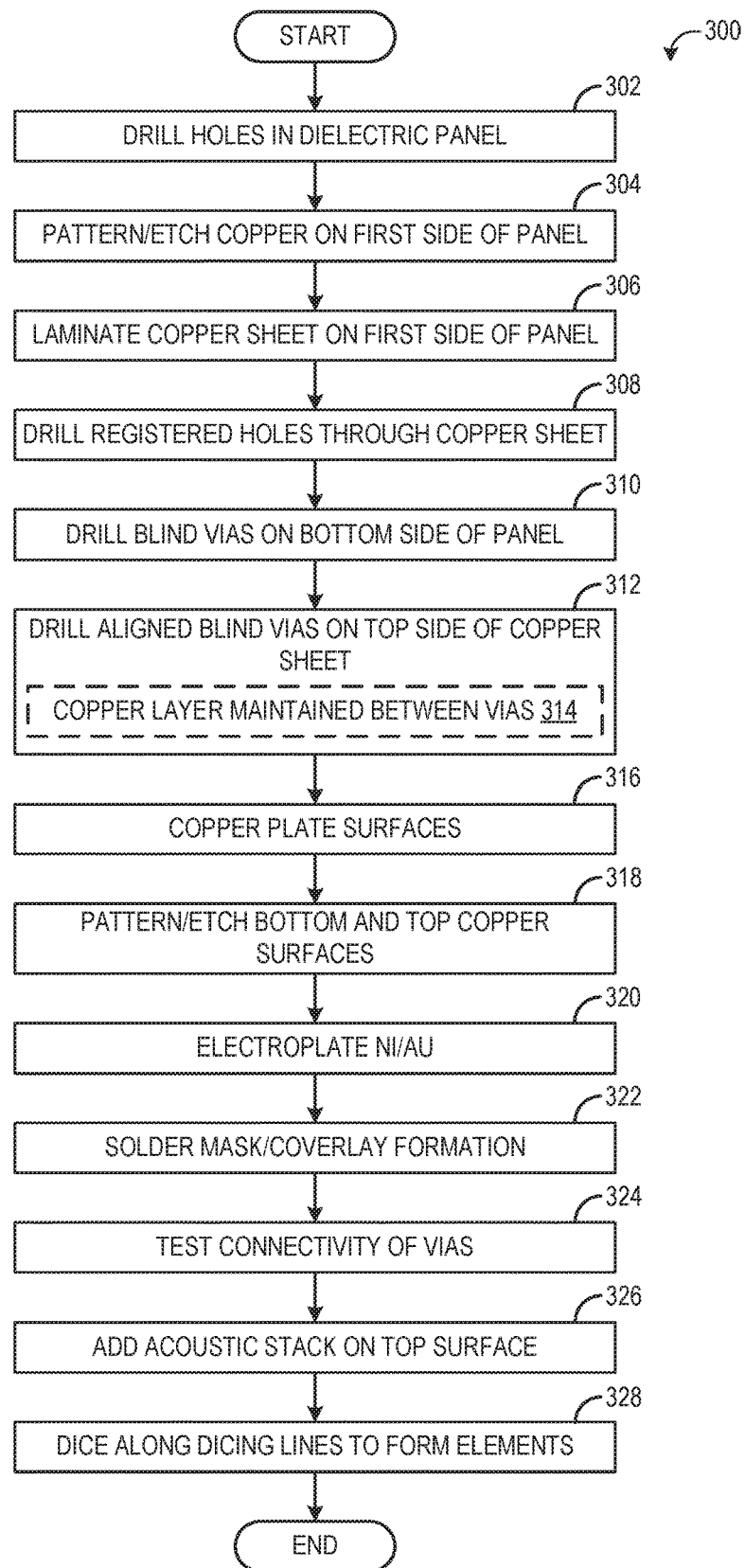
FIG. 3 shows a method for forming a flexible circuit for use in an ultrasound transducer array.
Figure 14:
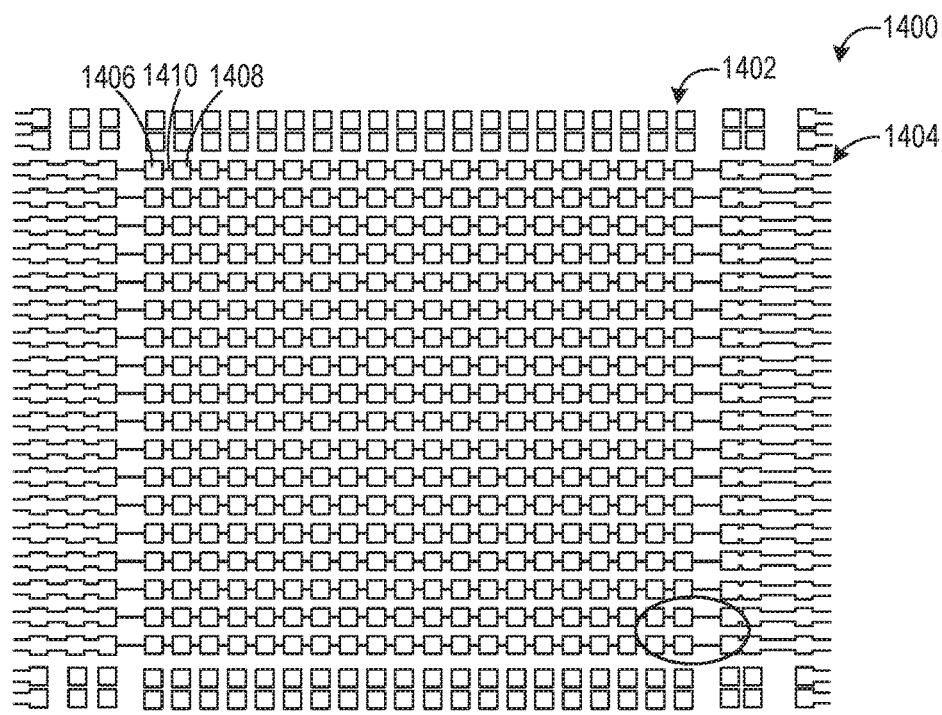
FIG. 14 shows a top-down view of an example flexible circuit formed in accordance with the method of FIG. 3.
Figure 15:
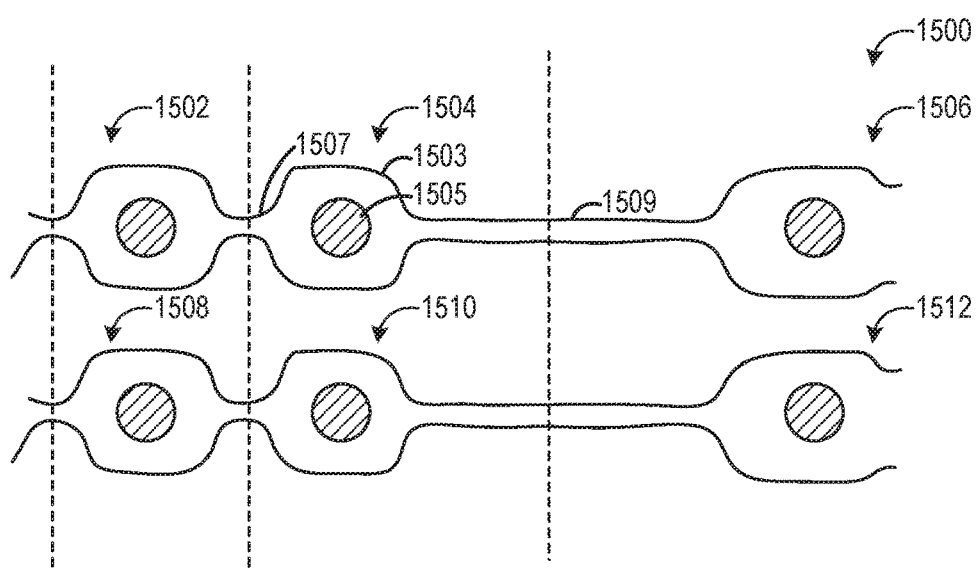
FIG. 15 is a magnified view of a portion of the flexible circuit of FIG. 13.
Figure 16:
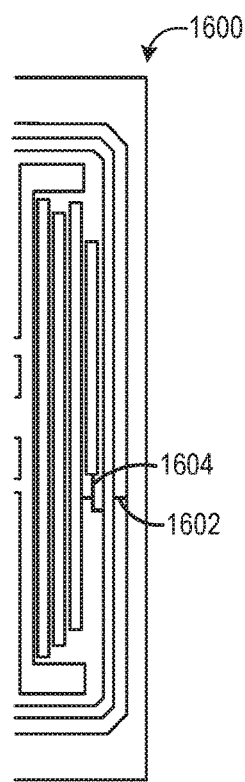
FIGS. 16 and 17 show additional views of the flexible circuit of FIG. 13.
Figure 17:
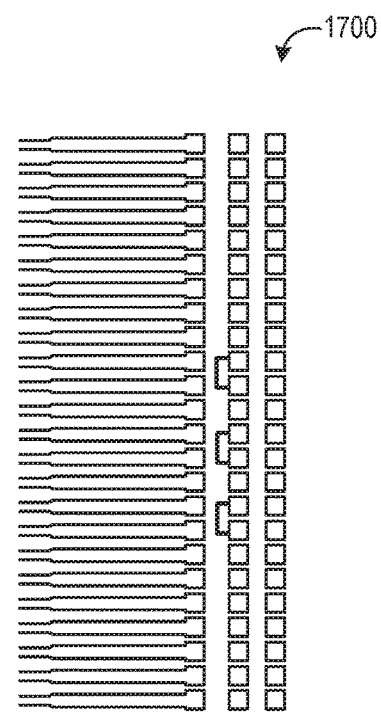

The following description relates to various embodiments of a flexible circuit that may be incorporated in a transducer array of an ultrasound probe, such as the ultrasound probe shown in FIG. 1. In particular, systems and methods are provided for forming a flexible circuit that includes electrical traces that allow for testing connectivity of a plurality of interconnects (also referred to as vias) of the flexible circuit before the flexible circuit is coupled to one or more transducers of the ultrasound probe. An example of a plurality of transducers of ultrasound probe is depicted in FIG. 2, showing components of the acoustic stacks that comprise the ultrasound transducers coupled to a flexible circuit. A flow chart illustrating a method for forming a flexible circuit for use in a transducer array, including testing the vias of the flexible circuit, is shown in FIG. 3. Cross-sectional views of the flexible circuit and/or transducer stack at various stages of the method of FIG. 3 are shown in FIGS. 4-13. A top-down view of a flexible circuit including the formed electrical traces is shown in FIG. 14, with FIG. 15 showing a magnified view of a portion of the flexible circuit of FIG. 14. FIGS. 16 and 17 show additional layers of the flexible circuit including electrical traces.

Turning now to FIG. 1, a block diagram of an ultrasound imaging system 100 according to one embodiment is illustrated. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric crystals, within an ultrasound probe 106 (or transducer) to emit pulsed ultrasonic signals into a body or volume (not shown) of a subject. Furthermore, the probe is outfitted with one or more actuators 105 capable of receiving signals from a system controller 116, as described further below, in order to output tactile feedback to the user. The elements 104, the one or more actuators 105, and the probe 106 may have a variety of geometries. In some examples, the one or more actuators 105 may be omitted.

The ultrasonic signals emitted by the elements 104 are back-scattered from structures in the body, for example, blood vessels and surrounding tissue, to produce echoes that return to said elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system controller (e.g., electronic controller) 116 of the system 100 includes a plurality of modules, which may be part of a single processing unit (e.g., processor) or distributed across multiple processing units. The system controller 116 is configured to control operation of the system 100. For example, the system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. In system 100, the image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the system controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables a user (e.g., an operator) to directly or indirectly control operation of the system 100 and the various components thereof. As shown, the user interface 122 includes a display device 118 having a display area 117. In some embodiments, the user interface 122 may also include one or more input devices 115, such as a physical keyboard, mouse, and/or touchpad. In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the system controller 116 to the operator by displaying the information to the operator. The display device 118 and/or the user interface 122 may also communicate audibly. The display device 118 is configured to present information to the operator during the imaging session. The information presented may include ultrasound images, graphical elements, user-selectable elements, and other information (e.g., administrative information, personal information of the patient, and the like).

FIG. 2 shows an example transducer array 200 comprised of a plurality of transducer elements 201. Transducer array 200 may be included in an ultrasound probe, such as probe 106 of FIG. 1, and thus the transducer elements 201 are non-limiting examples of elements 104 of FIG. 1. While FIG. 2 shows six transducer elements, it is to be understood that array 200 may include hundreds or thousands of transducer elements arranged into a linear or 2D array. The plurality of transducer elements 201 includes a first transducer element 202 and additional transducer elements that are configured similarly to transducer element 202. For simplicity, only transducer element 202 is described herein, but it is to be understood that the other transducer elements in the transducer array 200 may be configured similarly and the description of transducer element 202 likewise applies to the other transducer elements.

Transducer element 202 includes a piezoelectric layer 206 with at least one acoustic impedance dematching layer 208 and with a support layer 204 to form an acoustic stack. In some embodiments, the piezoelectric layer 206 may include lead zirconate titanate (PZT) and may be a single crystal PZT or multi crystal PZT. Non-limiting examples of the dematching layer includes dense, high modulus metals, such as molybdenum or tungsten, and high density ceramics, such as tungsten carbide. The dematching layer 208 has an acoustic impedance greater than that of the piezoelectric layer 206. For the configuration shown in FIG. 2, the support layer 204 may have an acoustic impedance between that of water and the piezoelectric layer 206. In some embodiments, the support layer 204 comprises a graphite support layer. Other candidate materials for support layer 204 include, without limitation, ceramics, silicon, flexible organic polymers, metal filled graphite, ceramic powder filled epoxy, glass, and glass-ceramics.

The acoustic stack (e.g., support layer 204, piezoelectric layer 206, and dematching layer 208) may be formed as a continuous block and coupled to a flexible circuit 216 (described below) in the continuous block. Then, after coupling to the flexible circuit, the acoustic stack may be diced into rectangles, for example, to form the individual transducer elements shown in FIG. 2. The transducer elements may be separated by kerfs that form from the dicing.

Transducer array 200 further includes a common ground electrode 214 coupled to each transducer element. For example, a suitable metal electrode may be attached to the support layer 204, along with an outer matching layer 212 attached to electrode 214, to provide a common ground electrode for all of the acoustic elements. Non-limiting examples of suitable materials for the outer matching layer 212 include ABS plastic, polyethylene, polystyrene, and unfilled epoxy. Other materials with similar acoustic impedances may be used as well. In some examples, electrode 214 and/or matching layer 212 may be diced along with the acoustic stack, or electrode 214 and/or matching layer 212 may be coupled after the acoustic stack has been diced. Further, in examples where the electrode is a common electrode coupled to multiple transducer elements, the electrode (and in some examples the matching layer) may be coupled to a subset of the transducer elements (e.g., 6, 10, 20 transducer elements), and thus the array 200 may include multiple electrodes and/or matching layers. While not shown in FIG. 2, it is to be understood that other elements are present in the transducer stack, such as electrodes on the bottom surface of each piezoelectric layer and through vias within each dematching layer to electrically couple the piezoelectric layer to an underlying flexible circuit.

Transducer element 202 is coupled to a flexible circuit 216. As shown in FIG. 2, the other transducer elements of the plurality of transducer elements 201 are also coupled to flexible circuit 216. Transducer element 202 (and the other transducer elements) is coupled to flexible circuit 216 via a suitable connection. As shown, transducer element 202 is coupled to flexible circuit 216 via an electric contact 210 that is coupled to a conductive pad 218 of flexible circuit 216. Electric contact 210 may comprise a suitable electrical connection, such as anisotropic conductive film (ACF), although other connections are possible, such as raised contacts (e.g., an under-bump metallization (UBM) deposited on the dematching layer 208 and a solder bump on the UBM). The ACF may be used to couple the acoustic stack to the flexible circuit before the acoustic stack is diced into the transducer elements. In some examples, the ACF may be diced along with the acoustic stack.

The transducer array 200 further includes an application specific integrated circuit (ASIC) die 220 coupled to flexible circuit 216. ASIC die 220 may be coupled to flexible circuit 216 using a suitable mechanism, such as anisotropic conductive film (ACF). While FIG. 2 only shows one die 220, it is to be understood that array 200 may include multiple die, with each die being operably coupled to one or more transducer elements (e.g., as shown, six transducer elements are operably coupled to die 220).

ASIC die 220 provides the acoustic sensor interface electronics, while flexible circuit 216 provides electrical interconnect from the ASIC die to the transducer array, as well as from the ASIC die to an external data processing system (not shown). Accordingly, flexible circuit 216 includes a plurality of vias, which are vertical interconnects, to electrically couple the transducer elements to the ASIC die, such as via 219 which extends from the top of flexible circuit 216 to the bottom of flexible circuit 216. As explained above, FIG. 2 only illustrates a subset of the transducer elements that may be present in array 200, and array 200 may include hundreds or thousands of transducer elements, each of which is coupled to an ASIC die with a via of flexible circuit 216. Accordingly, flexible circuit 216 may include hundreds or thousands of vias, which are electrically isolated from each other. As will be explained in more detail below, flexible circuit 216 may be formed from a plurality of patterned conductive layers and the vias may be formed by drilling holes through the plurality of conductive layers. Exposed surfaces of the flexible circuit are then plated with conductive material, thereby forming conductive vias though the flexible circuit. If any of the vias do not plate properly or are not drilled properly, conductivity through the vias may not be provided, which may lead to non-functional transducer elements, and possible reliability issues if connections are not robust. Thus, before laminating the acoustic stack on the flexible circuit, the connectivity of each via may be tested. However, performing connectivity checks of all the vias may be challenging. For example, an electrical connection through the vias may not be present until the ASIC dice are coupled to the bottom of the flexible circuit and the acoustic stacks are coupled to the top of the flexible circuit, at which point addressing any unconnected vias may be difficult. Further, the topography of the flexible circuit, and in particular the topography of the top surface of the flexible circuit, may pose challenges if one or more contact pads are not filled or planar. Accordingly, prior to coupling the acoustic stacks to the flexible circuit, the connectivity of the vias may be tested using a double-sided probe or using a temporary shorting plate. Such a testing configuration may pose challenges, as the double-sided probe or shorting plate may cause degradation of the flexible circuit or other issues.

Thus, according to embodiments disclosed herein and described in more detail below, flexible circuit 216 may be formed with electrical traces that electrically connect the vias to a source of electricity. In this way, the vias may electrically connect the layers of conductive material of the flexible circuit without the ASIC dice or acoustic stacks being present. This may allow easier testing of the connectivity of the vias prior to coupling of the ASIC dice and/or acoustic stacks. Further, surfaces of flexible circuit 216 may be plated with nickel and gold after copper plating. Typically, the nickel-gold plating may be performed using an electroless process, such as electroless nickel immersion gold plating (ENIG) or electroless nickel electroless palladium immersion gold plating (ENEPIG). However, given the presence of the electrical traces in the flexible circuit, the flexible circuit may be plated with nickel and gold using an electrolytic process, which requires the vias to be electrically conductive in order to be plated. Because the gold plating is a different color than the copper plating, if any of the vias do not plate with nickel and gold, the non-plated interconnects will have a different color than the plated interconnects, allowing for optical/visual inspection of non-connected interconnects. After the flexible circuit has been formed and tested for interconnect connectivity, the ASIC dice and acoustic stacks may be coupled to the flexible circuit. As explained above, the acoustic stacks may be coupled to the flexible circuit as a continuous block/set of layers and then diced to form the individual transducer elements. During dicing, at least some of the electrical traces in the flexible circuit may be cut or otherwise severed, which may then preserve the electrical isolation of the vias.

FIG. 3 illustrates a method 300 for forming a flexible circuit configured to couple to a transducer array for use in an ultrasound probe. For example, method 300 may be employed to produce the flexible circuit of the transducer array 200 of FIG. 2, which may be incorporated in the probe 106 of FIG. 1.

Figure 4:
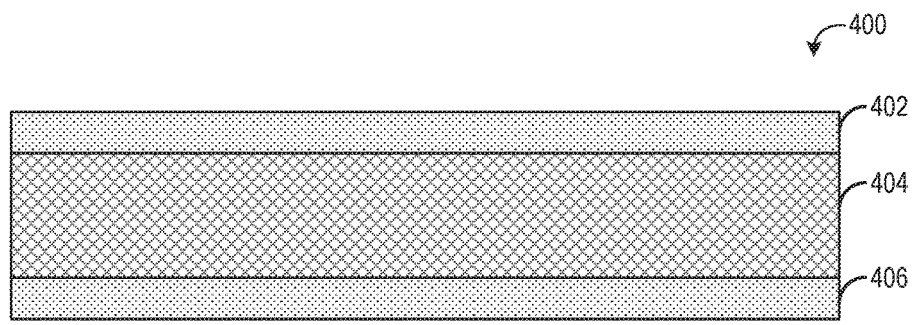
FIGS. 4-13 show cross-sectional views of a flexible circuit formed according to the method of FIG. 3, at various stages of the formation of the flexible circuit.
Figure 5:
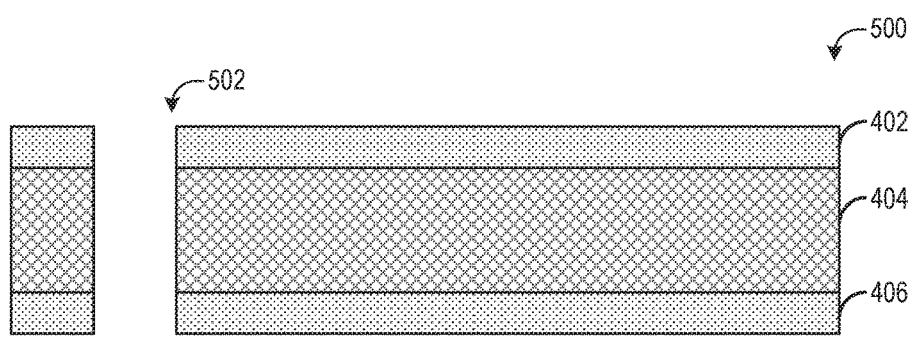

At 302, through holes are drilled in a dielectric panel. The dielectric panel may be comprised of an insulating material (such as polyimide or polyether ether ketone) coupled between two layers of a conductive material, such as copper. The holes may be drilled in the dielectric panel using laser ablation, plasma etching, or other suitable drilling technique. In some examples, a plurality of holes are drilled into the dielectric panel. FIG. 4 shows a cross-sectional view of an example dielectric panel 400 comprised of an insulating layer 404, a first copper layer 402, and a bottom copper layer 406. The overall thickness of the dielectric panel may be 50 μm, for example, and each copper layer may have a thickness of 5-10 μm. FIG. 5 shows the dielectric panel 400 of FIG. 4 in a drilled state 500, with a hole 502 drilled in the dielectric panel. The hole 502 may have a suitable width, such as 750 µm, and may extend across an entirety of the thickness of the dielectric panel (e.g., from the first copper layer 402 to the bottom copper layer 406).

Figure 6:
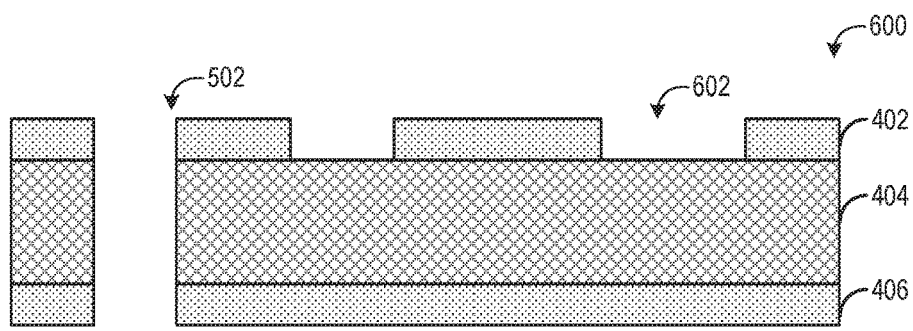

At 304, method 300 includes patterning/etching a desired pattern on the conductive material on a first side of the dielectric panel, for example the top side. The patterning/etching may be performed using a photolithography process, for example. FIG. 6 shows a patterned dielectric panel 600, with the drilled dielectric panel from FIG. 5 having undergone a patterning/etching process on the first copper layer 402. As a result, a pattern is formed in the first copper layer 402, including regions where the original copper plating has been removed (such as region 602), exposing the underlying insulating material.

Figure 7:
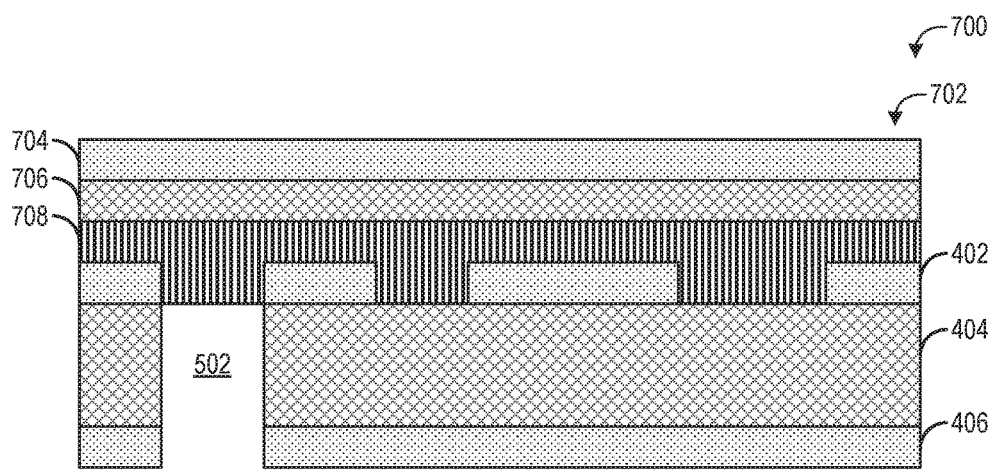

At 306, a copper sheet is laminated on the first side of the patterned, drilled dielectric panel. The copper sheet may include a layer of copper on an insulating layer, with a layer of adhesive on the bottom of the insulating layer. The adhesive layer may be used to laminate the insulating layer and layer of copper on the dielectric panel, thereby forming a multilayer flexible circuit panel. FIG. 7 shows an example multilayer flexible circuit panel 700, including the drilled, patterned dielectric panel of FIG. 6 laminated with a copper sheet 702. The copper sheet 702 includes an outer copper layer 704 on an insulating layer 706. The outer copper layer 704 may have a thickness in the range of 5-10 µm, for example, and the insulating layer 706 may also have a thickness in the range of 5-10 µm. The insulating layer 706 may be comprised of the same material as insulating layer 404, such as polyimide. The copper sheet 702 further includes an adhesive layer 708 that may couple the insulating layer 706 and outer copper layer 704 to the dielectric panel. When the adhesive layer is heated and/or pressed, the adhesive layer may fill in the gaps formed during the etching/patterning of the first copper layer 402. For example, region 602 (shown in FIG. 6) is filled with adhesive once the copper sheet 702 is laminated to the dielectric panel. Additionally, as shown in FIG. 7, the hole 502 is covered by the copper sheet 702, such that hole 502 is open on a bottom side but covered on a top side.

Figure 8:
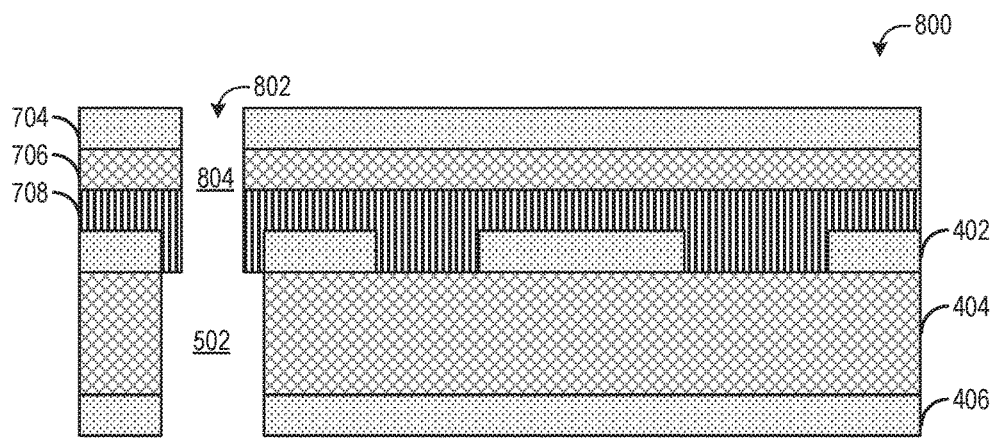

At 308, method 300 includes drilling holes through the copper sheet to form registered through holes. The copper sheet may be drilled (e.g., using laser ablation or plasma etching) where the copper sheet covers the holes drilled in the dielectric panel, such that through holes are formed. The holes thus extend from the outer copper layer of the copper sheet to the bottom copper layer of the dielectric panel. FIG. 8 shows a drilled multilayer flexible circuit panel 800 with a hole 802 formed by drilling a hole 804 that is registered with hole 502. Hole 804 may have a smaller diameter than hole 502, such as a diameter of 500 µm. In this way, hole 802 may include a region of no material (e.g., a void) that extends from outer copper layer 704, through insulating layer 706, adhesive layer 708, first copper layer 402, insulating layer 404, and bottom copper layer 406. However, because the diameter of hole 804 is less than the diameter of hole 502, surfaces of first copper layer 402 are not exposed in hole 802, but instead are covered by adhesive layer 708. By drilling hole 804 to have a smaller diameter than hole 502, a registration check of the separate drilled layers may be performed.

At 310, method 300 includes drilling blind vias on a bottom side of the dielectric panel. The blind vias may be drilled through the bottom copper layer and the insulating layer of the dielectric panel, terminating at a bottom surface of the first copper layer (that is now in the middle of the flexible circuit). The blind vias may be drilled at locations where electrical connection to an overlying acoustic stack (described in more detail below) is desired. At 312, method 300 includes drilling aligned blind vias through the copper sheet and to a top side of the first copper layer of the dielectric panel (e.g., to a top surface of the copper layer in the middle of the flexible circuit). Drilling the blind vias includes, as indicated at 314, maintaining the copper layer between the blind vias. For example, the middle copper layer of the flexible circuit is not drilled through when forming the blind vias.

Figure 9:
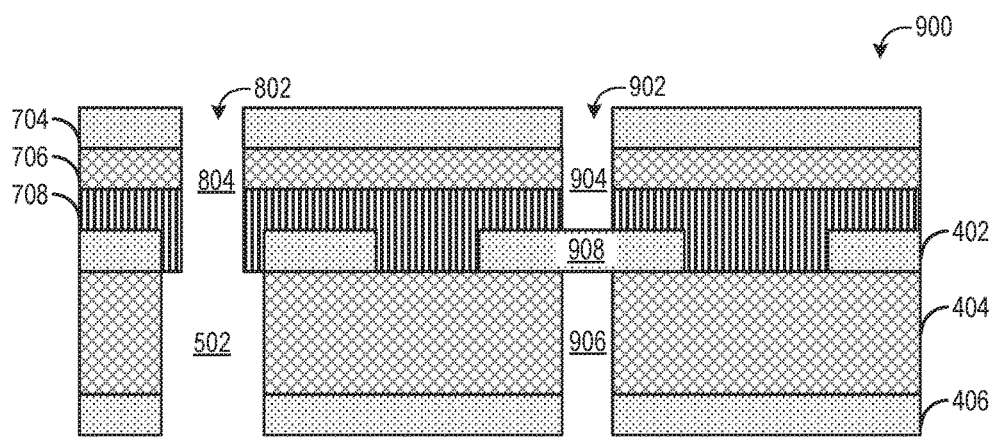

FIG. 9 is a cross-sectional view of a flexible circuit 900 with blind vias depicted in the multi-layer construction. The flexible circuit shown in FIG. 9 includes an aligned blind via 902 formed from a top blind via 904 and a bottom blind via 906. The top blind via 904 extends from the outer copper layer 704, through the insulating layer 706 and adhesive layer 708, terminating at the first copper layer 402. The bottom blind via 906 extends from the bottom copper layer 406 and through the insulating layer 404, terminating at the first copper layer 402. Each of the top blind via 904 and bottom blind via 906 may have a suitable diameter, such as 40 µm. The segment of the first copper layer 402 that spans the aligned blind via 902 forms a first intermediate layer 908. Aligned blind via 902 forms a via that creates an electrical connection from the top to the bottom of the multilayer flexible circuit, to create a connection from an overlying acoustic stack (described in more detail below) to an underlying ASIC chip. Each patterned trace in the central copper is either a through element connection or a routing trace that carries a surface conductor for passive elements, ground connections, and system connectors.

Figure 10:
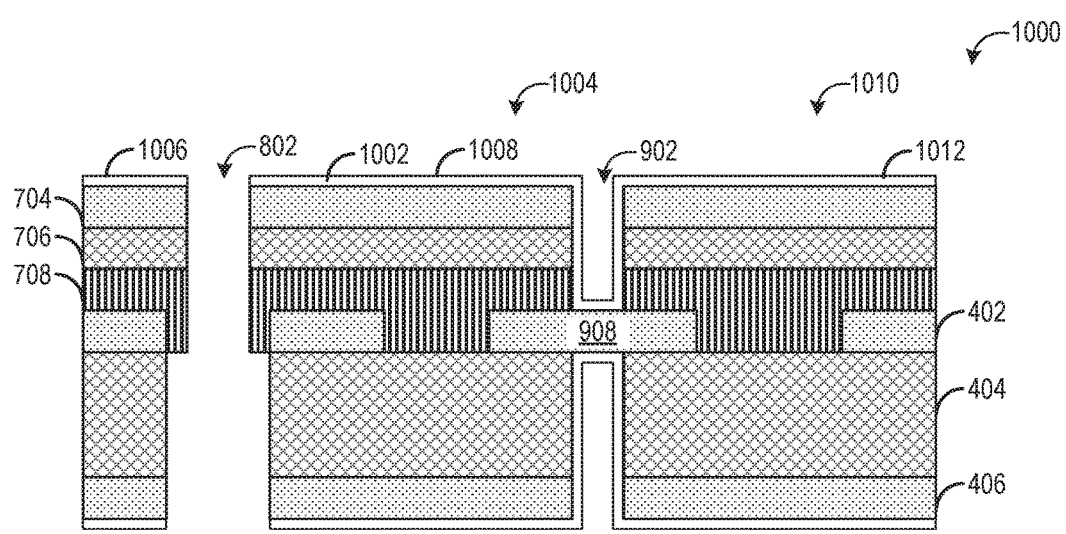

At 316, the exposed surfaces of the flexible circuit (e.g., the exposed surfaces of the copper sheet and dielectric panel, including exposed surfaces of the blind vias) are plated with copper. The copper may be plated using a suitable process, such as electroless plating (which may be followed by electroplating to ensure a robust coating of copper). For example, FIG. 10 shows a plated flexible circuit 1000, where the flexible circuit of FIG. 9 is plated with copper, and thus a plated layer of copper 1002 is formed on all exposed surfaces of the flexible circuit, including the top surfaces of the flexible circuit, bottom surfaces of the flexible circuit, and inner surfaces of the aligned blind vias (e.g., aligned blind via 902). Through hole 802 may not be plated.

Figure 11:
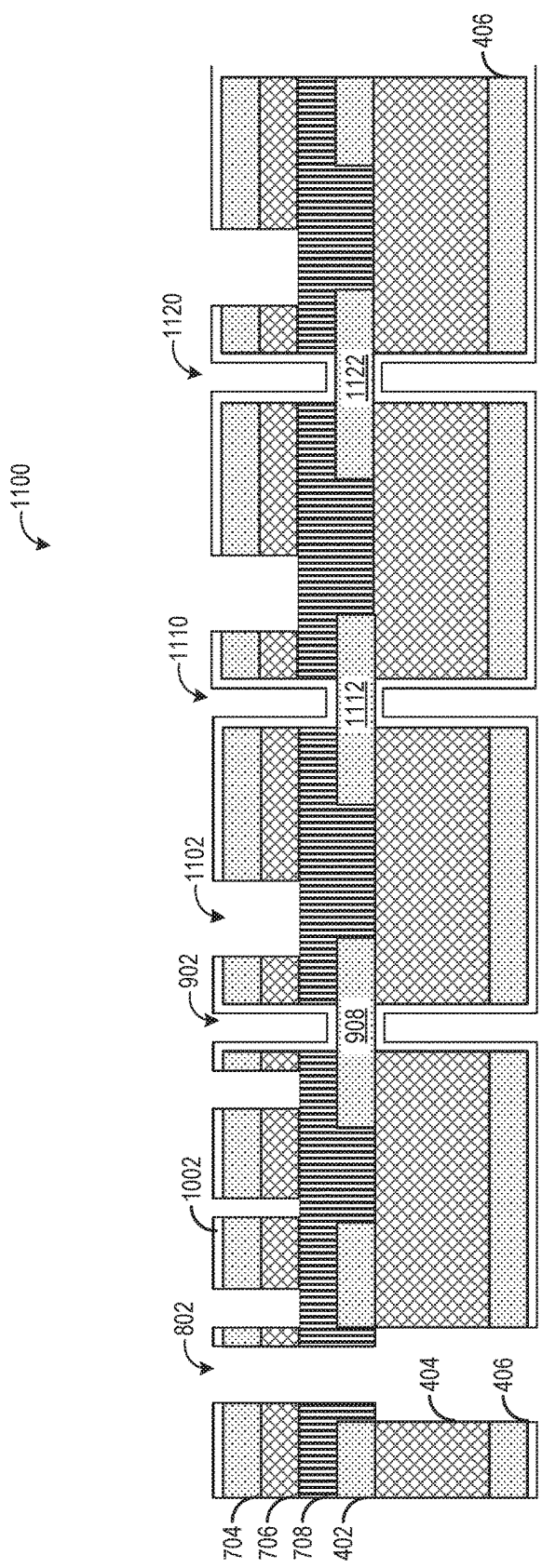

At 318, method 300 includes etching/patterning the outer copper layers of the flexible circuit (e.g., the bottom copper layer and top (outer) copper layer) according to a desired pattern. The patterning may be performed using photolithography or other suitable process, in order to form contact pads for accommodating the ASIC dice that will be positioned under the flexible circuit and provide desired connections/accommodations for the acoustic stack that will be coupled to the top of the flexible circuit. FIG. 11 shows a patterned flexible circuit 1100, where the flexible circuit of FIG. 10 has undergone the patterning/etching process on both the outer copper layer 704 and the bottom copper layer 406. In particular, the outer copper layer 704 and insulating layer 706 have both been etched/patterned, such that both the outer copper layer 704 and insulating layer 706 have been removed in some regions, such as region 1102, exposing the adhesive layer 708. On the bottom side, the bottom copper layer 406 may also be removed in some regions exposing the insulating layer 404. The patterning may provide for the formation of contact pads each including a blind via. Further, one of the layers (e.g., layer 406) may be patterned to include debus lines. As illustrated in FIG. 14, the flexible circuit may include a central array 1402 of contact pads formed according to the method described herein (e.g., blind vias drilled as described above and contact pads formed via the patterning as described above, where each contact pad includes a blind via). The central array 1402 may include a plurality of rows of contact pads, such as row 1404. Typically, each contact pad in a given row may be electrically isolated from one another, at least before the coupling of additional components to the flexible circuit. However, as shown in FIG. 14 and explained herein, each row may include a debus line, such as debus line 1410, that electrically couples each contact pad in that row (as well as to other components of the flexible circuit), such as contact pad 1406 and contact pad 1408. The debus lines may be formed via the patterning. For example, rather than patterning layer 406 to isolate each contact pad, the patterning may leave a line of layer 406 that extends between each contact pad of a given row.

Returning to FIG. 11, the view of the flexible circuit illustrated in FIG. 11 is an expanded view showing additional blind vias formed in the multilayer flexible circuit. For example, aligned blind via 902 may be a first blind via, and the circuit may include a second blind via 1110 including a second intermediate layer 1112 formed in the copper layer 402 and a third blind via 1120 including a third intermediate layer 1122 formed in the copper layer 402. It is to be understood that the flexible circuit may include hundreds or thousands of blind vias similar to those illustrated in FIG. 11, arranged into an array (e.g., arranged into multiple rows of blind vias).

The blind vias shown in FIG. 11 may be positioned in a central array of the flexible circuit, such as central array 1402, where the multiple connections of the acoustic elements are formed vertically through the flex to the ASIC. The vertical feeds throughs will be connected through the ASIC chip. The central layer (e.g., layer 402) routes the element signals from the center of the stack to the ends of the flex and are brought back up to the outer layers to make contact to connectors that bring the signals to the system and other support electronics.

At 320, the flexible circuit is plated with nickel and gold using an electroplating process. The electroplating process may include immersing the flexible circuit in an electrolyte that includes dissolved metal salts and ions to conduct electricity. The flexible circuit acts a cathode and the nickel (and then gold) to be plated is the anode, which is also immersed in the electrolyte. A power supply supplies a direct current to the anode, oxidizing the metal atoms that it comprises and allowing them to dissolve in the solution. At the flexible circuit, which is also supplied with current, the dissolved metal ions in the electrolyte solution are reduced at the interface between the solution and the flexible circuit, where they plate onto the flexible circuit in any regions that are electrically connected (and hence flow current). The process may be performed first to plate the nickel and then the process may be performed again to plate the gold on the nickel. Due to the debus lines connecting the contact pads of the flexible circuit (e.g., debus line 1410 of FIG. 14), the blind vias (such as blind via 902 of FIGS. 9-11) of the flexible circuit are conductive, and thus the inner surfaces of the vias will plate with nickel and gold if the vias are formed properly. If one or more of the vias are not formed properly, for example if the copper did not plate along an entirety of the surfaces of a via, or if the top copper layer or bottom copper layer do not contact the copper plating the inner surfaces of a via, those vias will not plate with nickel and gold during the electrolytic plating.

At 322, a coverlay and/or solder mask is formed on the flexible circuit to encapsulate the external circuit layers of the flexible circuit. For example, polyimide may be laminated to the outer surfaces of the flexible circuit. The contact pads or connection points may be exposed by photolighography, drilling, punching, etc., through the coverlay/solder mask. The coverlay/solder mask is then open at all electrical connections points for bonding and connection, at the central array elements that connect the acoustic stack to ASIC bond pads, passive component assembly pads (e.g., resistors, capacitors, inductors), and assembly pads for connectors.

At 324, the connectivity of the vias is tested. As explained above, the flexible circuit may be plated in nickel and gold using an electrolytic process, due to the presence of the debus lines electrically coupling the contact pads of the flexible circuit. If a via is not formed properly or otherwise does not electrically couple the top copper layer of the flexible circuit to the bottom copper layer of the flexible circuit, that via will not plate with nickel and gold and instead the copper plating will be visible. Due to the color difference between gold and copper, a via that has not plated with gold can be detected via an optical/visual test. For example, an RGB camera or other image sensor may be used to image the flexible circuit and computer vision/image recognition may be performed to detect if any vias did not plate with gold. In another example, a user may perform a visual inspection to determine if any vias did not plate with gold. If the flexible circuit includes any vias that did not plate with gold, the flexible circuit may be discarded, or the flexible circuit may be modified to attempt to fix any issues leading to the non-connected via. The connectivity may be determined through multiple test points in the process, such as post FPC fabrication. There is also some level of testing post ASIC attachment with temporary connections of the FPC enabled. These two gates may enable streamlined product and assembly cost reductions from less scrap generation. Parts can be screened prior to attaching the ASICs as well as prior to attaching the acoustic stack layers. The post FPC test is visual for non-plating and an electrical automated flying probe test may be performed that can test for opens (however, the presence of the debus lines creates shorted elements so only specific nets or adjacency can be tested for shorting). The post ASIC attachment allows for additional testing from an automated tester that allows for basic ASIC connectivity verification and certain evaluation of specific nets.

At 326, an acoustic stack is added to the flexible circuit. The acoustic stack may include an acoustic element, such as a piezoelectric layer, that is configured to generate an electrical charge in response to mechanical stress (e.g., from acoustic waves impinging on the element) and conversely output acoustic waves when supplied with an electrical charge. The acoustic element may be coupled to a matching layer, backing/dematching layer, ground electrode, etc., as explained above with respect to FIG. 2. The acoustic element may be electrically coupled to the vias in the flexible circuit upon addition of the acoustic stack to the flexible circuit. For example, the backing/dematching layer of the acoustic stack may include electrical connections (e.g., vias) that extend through the backing/dematching layer to the respective vias of the flexible circuit.

Figure 12:
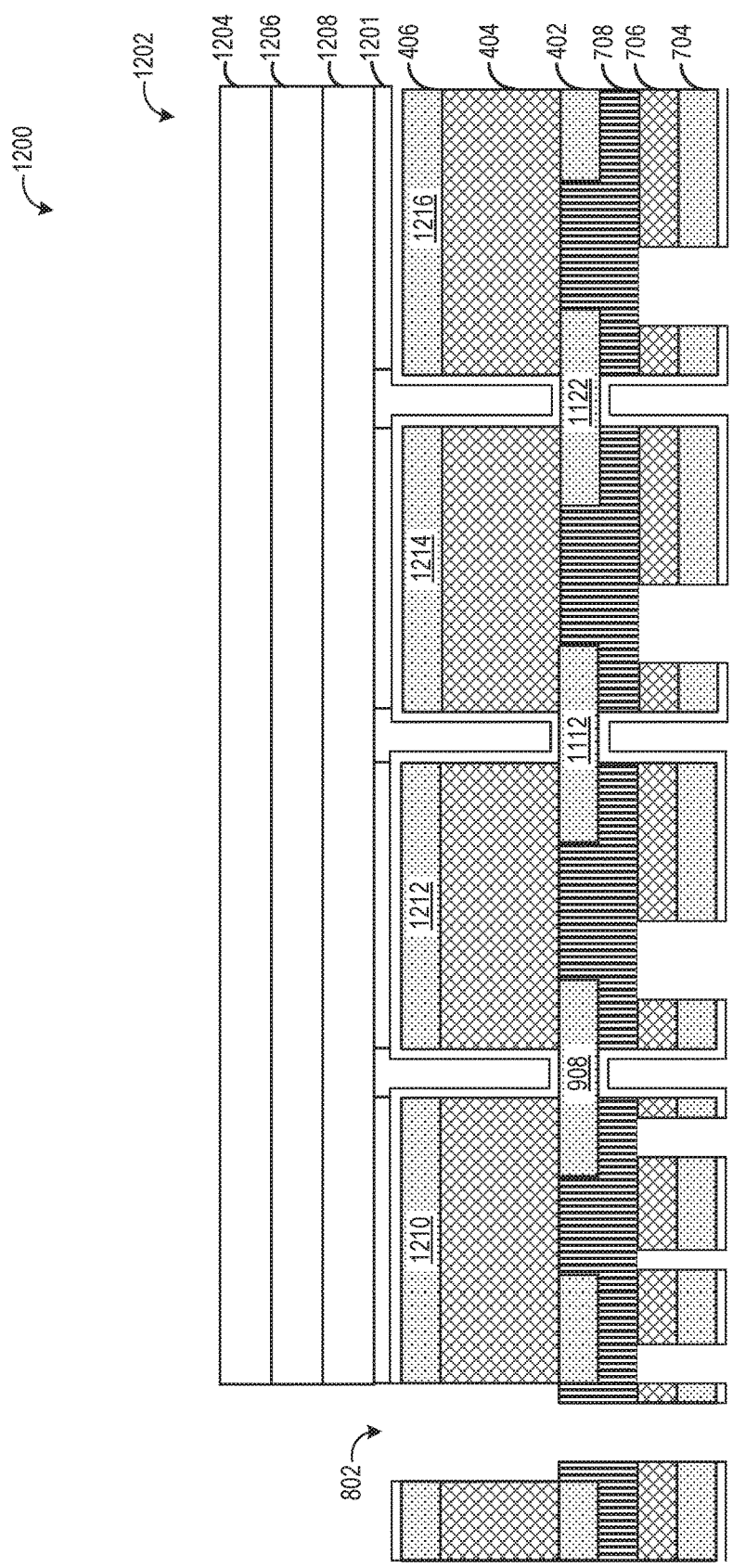

FIG. 12 shows an example flexible circuit/acoustic stack in a first configuration 1200, which includes the flexible circuit of FIG. 11 (after nickel/gold plating, coverlay formation, and testing to confirm connectivity of the vias) with an acoustic stack 1202 coupled to (e.g., on coverlay 1201).

It will be appreciated that the orientation of the flexible circuit board is flipped in FIG. 12 relative to FIG. 11, such that layer 406 is on the top and layer 704 is on the bottom. Additionally, a debus line is shown in FIG. 12, being formed from segments of layer 406, including segment 1210, segment 1212, segment 1214, and segment 1216. In this way, segment 1212 may connect blind via 902 with blind via 1110, segment 1214 may connect blind via 1110 with blind via 1120, etc. The acoustic stack 1202 is positioned on top of layer 406. The acoustic stack 1202 includes a support layer 1204, piezoelectric layer 1206, and a dematching layer 1208, as explained above with respect to FIG. 2. The dematching layer may include vias or other connection through which electrical connection between the piezoelectric layer 1206 and the blind vias of the flexible circuit are established. However, other configurations for the acoustic stack are possible. The acoustic stack 1202 extends continuously across the flexible circuit, such that blind vias 902, 1110, and 1120 are covered by the acoustic stack.

Returning to FIG. 3, method 300 includes dicing the acoustic stack along a plurality of dicing lines to form individual transducer elements. The acoustic stack may be diced to form kerfs between the individual transducer elements. The acoustic stack may be diced in two directions. A first plurality of dicing lines may extend along parallel axes that extend from one side of the acoustic stack to an opposite second side of the acoustic stack. A second plurality of dicing lines may extend along parallel axes that are perpendicular to the first plurality of dicing lines, and may extend from a third side of the acoustic stack to an opposite fourth side of the acoustic stack. The dicing may cut through the acoustic stack, from the support layer, through the acoustic element layer and the dematching layer. Further, for one of the sets of dicing lines (e.g., either the first plurality or second plurality of dicing lines), the dicing may continue through the coverlay/solder mask 1201, through layer 406, and partially into layer 404, thereby to electrically isolate each contact pad and enable individual transducer element control and signal reception. The acoustic stack and traces may be cut using a suitable dicing saw, or another isolation method which can include laser profile, chemical etching, or plasma processing.

Figure 13:
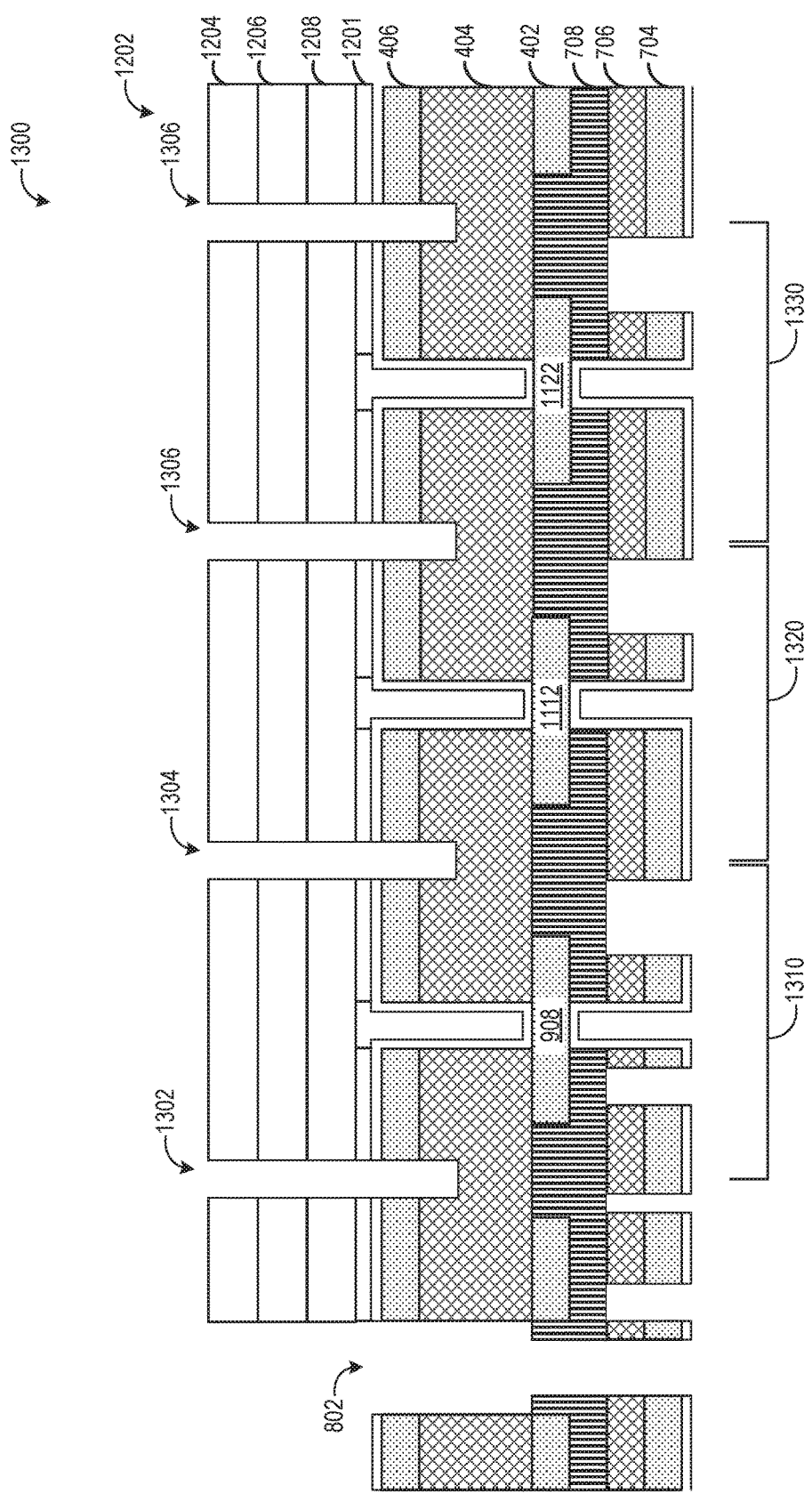

FIG. 13 shows an example flexible circuit/acoustic stack in a second, diced configuration 1300, where the flexible circuit/acoustic stack of FIG. 12 has been diced to form individual transducer elements. The dicing forms kerfs, such as kerf 1302, between the transducer elements. Kerf 1302 extends through the copper layer 406 of the flexible circuit, such that segment 1210 is cut. Likewise, kerf 1304 extends through copper layer 406, such that segment 1212 is cut and is thus no longer providing a connection between a first contact pad (e.g., that includes blind via 902) and a second contact pad of the flexible circuit (e.g., that includes blind via 1110). However, the dicing of the acoustic stack in the other, perpendicular direction, may not extend past the top of the flexible circuit. In this way, the dicing penetrates the piezo stack and the topside metal of the flex circuit. The dicing stops in the top dielectric layer. The dicing does not go through the entire flex circuit, and is a controlled depth cut.

When the segments of the debus line/copper layer 406 are cut, at least some of the surfaces of the segments of copper layer 406 that face into a respective kerf are not plated with copper, nickel, or gold. Because the debus line was uncut during copper plating and during nickel and gold plating, the top surface and bottom surface of the debus line may be plated in copper, nickel, and gold, but the interior of the debus line is comprised only of copper. When the debus line is cut, the interior of the debus line is exposed and is free from nickel and gold plating. Accordingly, after dicing, a gap (e.g., kerf 1304) is formed electrically separating the first contact pad from the second contact pad (and separating individual transducer elements).

Thus, upon dicing, a first contact pad 1310 and a second contact pad 1320 are partially separated from each other by a gap (e.g., kerf 1304), and the second contact pad 1320 and a third contact pad 1330 are partially separated by another gap (e.g., kerf 1306). Each contact pad includes a respective first conductive layer (layer 406), a respective second conductive layer (layer 402), a respective third conductive layer (layer 704), and a respective blind via extending through the first conductive layer and the third conductive layer (e.g., blind 902, blind via 1110, and blind via 1120). At the gap, the first conductive layer of the first contact pad and the first conductive layer of the second contact pad form an interrupted conductive path between the first contact pad and the second contact pad. The interrupted conductive path is comprised of a segment of layer 406, e.g., segment 1212, that is cut or otherwise severed. After dicing, the interrupted conductive path is made of a first segment and a second segment separated by the gap, the first segment comprising the first conductive layer of the first conductive pad and terminating at the gap and the second segment comprising the first conductive layer of the second conductive pad and terminating at the gap, where the first and second segments are co-planar. A first transducer element is coupled to a top surface of the first contact pad and a second transducer element coupled to a top surface of the second contact pad, and at least one application specific integrated chip is configured to couple to a bottom surface of the first contact pad and a bottom surface of the second contact pad.

A magnified view 1500 of a portion of flexible circuit 1400 is shown in FIG. 15. In the magnified view, a first contact pad 1502, a second contact pad 1504, and a third contact pad 1506 are arranged in a row, and a fourth contact pad 1508, a fifth contact pad 1510, and a sixth contact pad 1512 are arranged in a second row. Each contact pad includes a plated (e.g., with copper and with nickel and gold) via surrounded by a pad substrate. The pad substrate includes layers of conductive material (e.g., copper) and insulator. For example, second contact pad 1504 includes a via 1505 surrounded by a pad substrate 1503. Each contact pad is coupled to adjacent conductive pads in that pad's row by a debus line (e.g., electrical traces). For example, second contact pad 1504 is coupled to first contact pad 1502 by trace 1507 and second contact pad 1504 is coupled to third contact pad 1506 by trace 1509. The traces coupling adjacent contact pads allow electricity provided to the corners/surfaces of the flexible circuit during electroplating to flow though all of the vias of the flexible circuit, and thus the vias may be plated with nickel and gold. If any vias do not plate, as explained above, those vias will be of a different color (e.g., copper colored) than the other vias that did plate (which will be gold colored), which may allow for rapid detection of degraded/non-fully formed vias. After connectivity testing, the traces may be cut along suitable dicing lines, such as the dashed lines shown in FIG. 15, at the same time the acoustic stack is diced to form the individual transducer elements.

Electric traces may be present in other portions of the flexible circuit. For example, FIGS. 16 and 17 show traces that may be cut after connectivity testing. FIG. 16 shows bus lines 1600 that may be present in an internal layer of the flexible circuit. Traces 1602 and 1604 may be added to connect a few of the bus lines in order to enable the flow electricity during electroplating. After connectivity testing, these traces may be cut. FIG. 17 shows a set of conductive pads 1700 present in an internal layer of the flexible circuit with additional traces coupling adjacent conductive pads.

In this way, the disclosure provided herein allows for testing and inspection of high density vertical interconnect structures, including fabrication of the high density vertical interconnect structures, testing of the interconnects, and isolation of the contact pads. This disclosure also allows for added test capability of direct ASIC attachment to the flexible substrate that enables the sub-assembly to be screened prior to completing the entire acoustic laminate structure. The fabrication process includes electrolytic plating metal processing using a bus approach.

This disclosure provides for simplified testing of direct vertical interconnect structure that previously had to be performed by applying a temporary shorting plate or double-sided probing. The disclosure also allows for a more controlled electrolytic finish plating by using a bus connection process. The bus removal is done with an in situ process step that currently isolates acoustic materials forming isolated elements for acoustic sensing.

The configurations described herein allow for known good flexible substrate material to be utilized in the fabrication of an acoustic probe. The disclosure also allows for added test capability of ASIC to flexible substrate attachment that was previously limited in what could be tested. Previous flexible circuit configurations fabricated using ENIG or ENIPIG plating finishes do not allow for via visual inspection as described herein, as traditional automated optical inspection cannot determine if vertical interconnects are good. The bus process described herein allows for visual inspection of plated metal on the bottom side of the circuit indicating vertical interconnection. In doing so, a higher yield of probes may be obtained, each with a known good tested flex for assembly. Further, the flexible circuits described herein have increased ductility and elongation of the finish metal.

The nickel gold bus plating (NGB) plating of nickel gold surfaces described herein utilizes connectorized "bus" plating. The NGB bus design is to connect all top central array pads as well as a few features with temporary metal shorting traces and connect bottom pads through vias. This process enables a visual check post plating that the via interconnections have been made. Those short traces are laser cut during debus and acoustic stack dicing processes.

FIGS. 2 and 4-17 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

A technical effect of manufacturing a flexible circuit with traces coupling adjacent contact pads is the ability to electroplate nickel and gold rather than relying on an electroless plating process, which may be time-consuming and wasteful. Another technical effect is the ability to visually confirm the connectivity of vias of the flexible circuit without having to couple shorting plates or electrical clips to the flexible circuit.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A flexible circuit, comprising: a first contact pad; and a second contact pad partially separated from the first contact pad by a gap, each contact pad comprising a first conductive layer, a second conductive layer, a third conductive layer, and a blind via extending through the first conductive layer and the third conductive layer, and at the gap, the first conductive layer of the first contact pad and the first conductive layer of the second contact pad form an interrupted conductive path between the first contact pad and the second contact pad, wherein the interrupted conductive path includes a first segment and a second segment separated by the gap, the first segment comprising the first conductive layer of the first conductive pad and terminating at the gap and the second segment comprising the first conductive layer of the second contact pad and terminating at the gap, wherein the first and second segments are co-planar.

2. The flexible circuit of claim 1, wherein each blind via includes a plating of at least a first material and a second material.

3. The flexible circuit of claim 1, further comprising a first transducer element coupled to a top surface of the first contact pad and a second transducer element coupled to a top surface of the second contact pad.

4. The flexible circuit of claim 1, further comprising at least one application specific integrated chip coupled to a bottom surface of the first contact pad and a bottom surface of the second contact pad.

* * * * *